United States Patent [19]
Choi

[11] Patent Number: 5,129,914
[45] Date of Patent: Jul. 14, 1992

[54] ACUPUNCTURE NEEDLE CONTAINER AND INSERTION TUBE

[76] Inventor: Jeung H. Choi, 3409 W. Burbank Blvd., Burbank, Calif. 91505

[21] Appl. No.: 598,149

[22] Filed: Oct. 16, 1990

[51] Int. Cl.⁵ ............................................. A61B 17/34
[52] U.S. Cl. .................................... 606/189; 221/281; 221/312 R
[58] Field of Search ............... 606/182, 183, 181, 185, 606/189; 604/62; 206/366; 221/281, 312 R, 312 B, 312 C

[56] References Cited

U.S. PATENT DOCUMENTS

| | | |
|---|---|---|
| 505,645 | 9/1893 | Wolff . |
| 3,305,084 | 2/1967 | Higgins et al. .................. 206/366 |
| 3,494,458 | 2/1970 | Meierhoefer .................. 206/366 |
| 3,858,722 | 1/1975 | Haas . |
| 4,116,333 | 9/1978 | Pavel . |
| 4,488,343 | 12/1984 | dinh Can . |
| 4,518,384 | 5/1985 | Tarello et al. .................. 604/62 X |

FOREIGN PATENT DOCUMENTS 3522855 3/1986 Fed. Rep. of Germany ...... 606/189

Primary Examiner—Michael H. Thaler
Attorney, Agent, or Firm—Richard C. Litman

[57] ABSTRACT

A combination container and dispenser and insertion tube for acupuncture needles provides for the sterile storage and containment, dispensing and insertion of acupuncture needles. A storage portion of the container/dispenser is formed with an insertion tube along one edge and an internal passage between the two components. A lot in the storage portion allows manipulation of the handles of any acupunture needles within so they may be transferred through the internal passage to the insertion tube and inserted into the patient. A series of depressions and a retaining crest within the storage portion assist in retaining the needles in position until they are maneuvered through the slot. The device may be formed of a relatively inexpensive material, thus allowing for disposal after a single use, or alternatively may be formed of a more durable material capable of withstanding repeated sterilization in an autoclave or similar apparatus for reuse.

6 Claims, 1 Drawing Sheet

ACUPUNCTURE NEEDLE CONTAINER AND INSERTION TUBE

FIELD OF THE INVENTION

This invention relates generally to storage containers for needles used in medical practice and the like, and more specifically to a combination needle storage container and insertion tube for specialized needles used in the acupuncture field.

BACKGROUND OF THE INVENTION

Acupuncture needles are quite unlike other needles used in the medical field, and as a result require quite different handling. Typically, acupuncture needles are somewhat smaller and thinner than other needles used in the medical field, such as hypodermic needles. Moreover, hypodermic needles must include a fitting at one end for attachment to a syringe. This, in combination with the requirement for a hollow needle, results in a somewhat larger device than the typical acupuncture needle.

The standard practice in the acupuncture field is to use a needle insertion tube in order to aid the acupuncturist in the precise placement of the acupuncture needle. Whether the needle be disposable or reusable, the procedure is much the same. The needle is first removed from a sterile storage container by hand and installed within a separate insertion tube for placement into the patient. The insertion tube is then placed at the desired location on the patient, and the needle is pushed through the insertion tube into the patient. This procedure requiring the transferal of the needle from one device to another prior to use, results in a considerable amount of handling of the needle prior to use and thereby increases the chances for contamination of the needle. While such a procedure may be essential in the handling of a hypodermic needle which must be attached to a syringe prior to use, it is not seen to be the optimum procedure for use with acupuncture needles.

The need arises for a device which is capable of containing several acupuncture needles in a sterile environment, and also allowing those needles to be dispensed singly as desired by the acupuncturist. The device should provide for a minimum of handling of the needles, particularly the needle tip. Such an acupuncture needle storage and dispensing device should be made of inexpensive materials in order to allow for single use and disposal, or alternatively of materials sufficiently durable to permit sterilization within an autoclave or like device. The device should preferably be formed of a single component in order to provide for more efficient sterilization in the case of a reusable device.

DESCRIPTION OF THE RELATED ART

A. J. Wolff U.S. Pat. No. 505,645 discloses a case for hypodermic syringes. This device is relatively complex, in that it comprises several components. Moreover, no means is provided for the dispensing and/or application of the syringe needle to the patient.

R. V. Haas U.S. Pat. No. 3,858,722 discloses a device for the dispensing of needles or like objects. The needles must first be placed laterally along a tape, which is then rolled and installed within the dispenser. This device is not intended or suitable for applications in which the needles must be kept sterile, due to the possibility of contamination from the tape.

K. Pavel U.S. Pat. No. 4,116,333 discloses a dispenser for sewing machine needles or the like. This device is formed of a plurality of components, and at least two components must be rotated relative to one another in order to provide for the release of a needle from the device.

T. dinh Can U.S. Pat. No. 4,488,393 discloses a method of packaging sterile acupuncture needles. The needles are packaged in a manner similar to that of the Haas patent cited above. While this patent relates directly to acupuncture needles, no provision is made for the application of the needles directly from the storage package. Rather, each needle must be removed separately from its packaging and then inserted within an application tube and applied, as is known in the art.

None of the above noted patents, either singly or in combination, are seen to disclose the specific arrangement of concepts disclosed by the present invention.

SUMMARY OF THE INVENTION

By the present invention, an improved device for the storage and insertion of needles used in the acupuncture field is disclosed.

Accordingly, one of the objects of the present invention is to provide an improved acupuncture needle storage and insertion device which is capable of both containing sterilized acupuncture needles and singly dispensing and inserting such needles through an inserting tube for application to the patient.

Another of the objects of the present invention is to provide an acupuncture needle storage and insertion device which is formed as a single component, thus providing for better sterilization of the device.

Yet another of the objects of the present invention is to provide an acupuncture needle storage and insertion device which is reusable and which may be sterilized in much the same manner as other devices used in the medical field.

Still another of the objects of the present invention is to provide an acupuncture needle storage and insertion device of sufficiently economical manufacture to permit disposal after a single use.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

Similar reference characters designate corresponding parts throughout the several figures of the drawings.

DESCRIPTION OF THE PREFERRED EMBODIMENT

Figure 1:
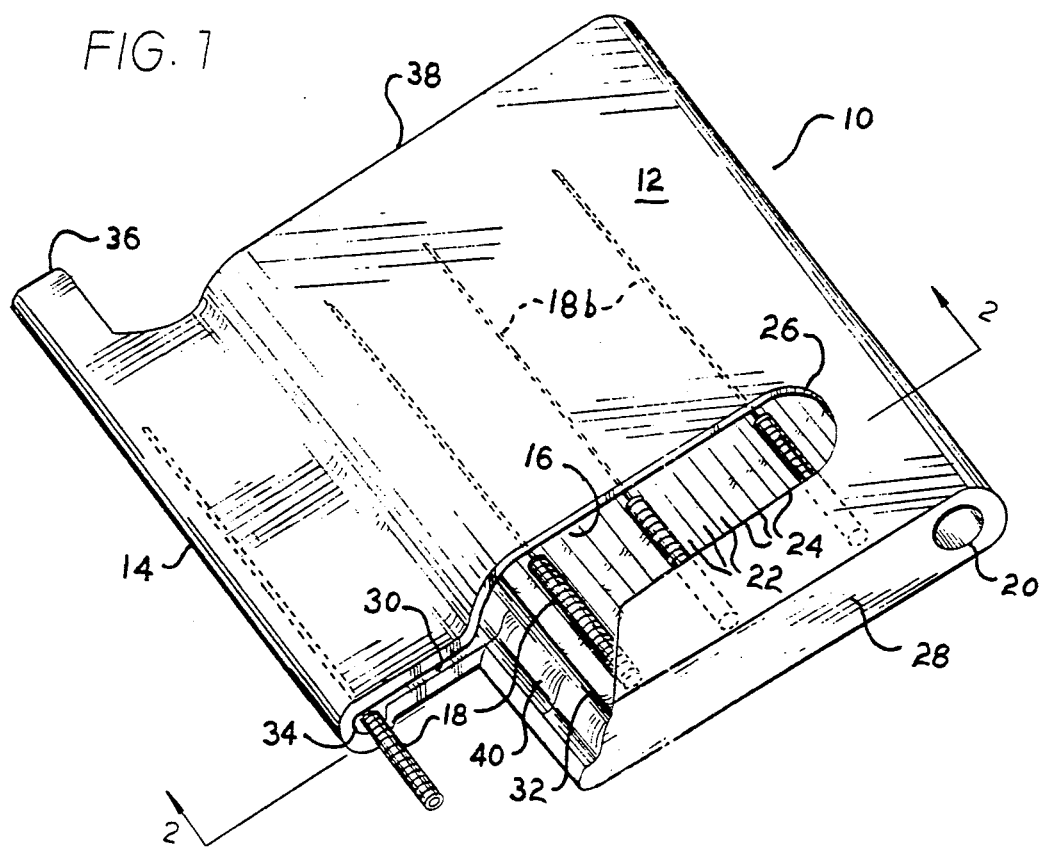
FIG. 1 is a top perspective view of the device, showing the general configuration and showing how acupuncture needles may be positioned therein.

Referring now to the drawings, particularly FIG. 1 of the drawings, the present invention will be seen to relate to a combination storage container, dispenser and insertion tube for acupuncture needles. Container/dispenser 10 includes a relatively flat storage portion 12 with a cylindrical insertion tube portion 14 conjoined along and parallel to one edge of storage portion 12.

Storage portion 12 and insertion tube portion 14 comprising container/dispenser 10 are preferably formed as a single unit, without seams, crevices or the like in order to permit ease of sterilization of the device. Container/dispenser 10 may be formed of any suitable material, such as a relatively inexpensive plastic or the like in order to permit the economical disposal thereof when the needle supply is depleted, or alternatively may be formed of a more durable material such as stainless steel to permit sterilization in an autoclave or by similar means as is well known in the art.

Storage portion 12 contains a receptacle 16 within for the containment and storage of any acupuncture needles 18 which may be contained therein. Receptacle 16 is relatively flat and of sufficient internal length to permit a plurality of needles 18 to be installed therein with their longitudinal axes parallel to one another, in a single layer. An opening 20 is provided near the edge of storage portion 12 opposite insertion tube portion 14 for the installation of any needles 18 within receptacle 16.

In order to prevent the movement of needles 18 within receptacle 16, a series of parallel longitudinal depressions 22 are located on the bottom of receptacle 16. Parallel ridges 24 separate each depression 22. The depth of receptacle 16 from the top of ridges 24 to the inside of the overlying top of storage portion 12 is sufficient to allow the passage of the largest diameter portion or handle 18a of any needles 18 contained therein from one depression 22 to the next with some manipulation.

A slot 26 is located in the upper surface of storage portion 12 near the installation end 28 containing needle installation opening 20. Slot 26 extends nearly the full width of storage portion 20 and provides access to the handle portion 18a of any needles 18 contained therein.

Figure 2:
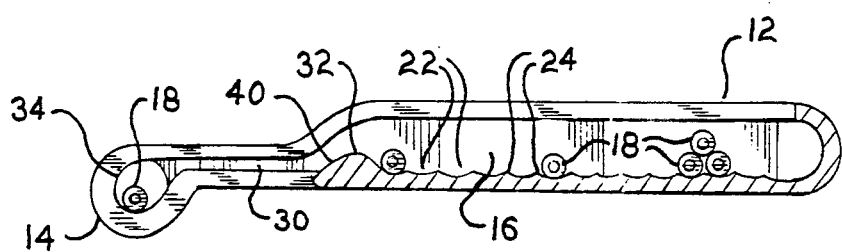
FIG. 2 is an end view in section, through section 2—2 of FIG. 1.
Figure 3:
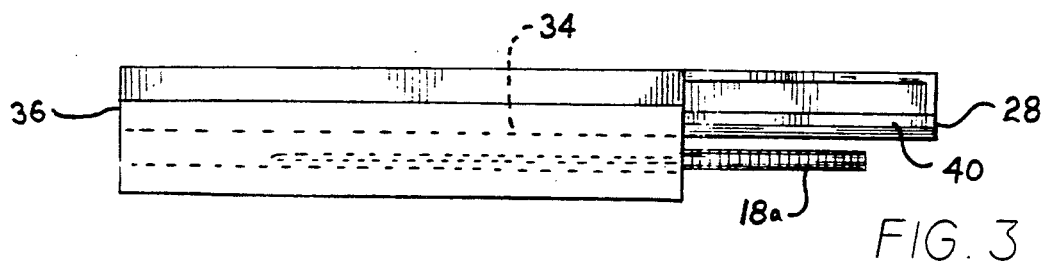
FIG. 3 is a side view of the device.

In order to further restrict the possible movement of needles 18 from within storage portion 12 to insertion tube 14, a relatively narrow passage 30 extends from storage portion 12 to the interior 34 of insertion tube 14. Passage 30 is only sufficiently wide to permit the lateral passage of the shaft portion 18b of any acupuncture needles 18 stored within receptacle 16. A relatively high crest 32, more clearly shown in FIG. 2, between receptacle 16 and the interior of insertion portion 14 assists further in preventing the unwanted dispensing of any needles 18.

The interior 34 of insertion tube portion 14 is of sufficient diameter to allow the passage of the largest diameter or handle portion 18a of an acupuncture needle 18 to pass therethrough. The dispensing end 36 of insertion tube 14 preferably extends somewhat beyond the enclosed end of container/dispenser 10 in order to permit the acupuncture specialist to more easily and precisely position the dispensing end 36 of insertion tube 14.

Acupuncture needle container/dispenser 10 is prepared for use by sterilization of container/dispenser 10 and any needles 18 installed therein. Alternatively, needles 18 may be sterilized before installation within container/dispenser 10, and installed by inserting the shaft end 18b of needles 18 into opening 20 and passing needle 18 completely into receptacle 16. Each needle 18 thus inserted may be advanced toward insertion tube portion 14 of container/dispenser 10 by manipulating the handle portion 18a of the needle 18 through slot 26, thus allowing space at opening 20 for the insertion of the next needle 18. Each needle 18 is positioned within a depression 22 within receptacle 16.

The first needle 18 installed within container/dispenser 10 will thus be closest to insertion tube 14. This first needle 18 may be maneuvered into position within insertion tube 14 by manipulating the needle 18 by the access provided through the slot 26 in order to cause the handle portion 18a of the needle 18 to pass across the last needle retaining depression 22 closest to passage 30, and thus shaft portion 18b to pass over crest 32 and into passage 30. Handle portion 18a may then be maneuvered down ramp 40, which provides a slope parallel to the initial portion of passage 30, to position shaft portion 18b within the interior 34 of insertion tube portion 14 of container/dispenser 10.

Container/dispenser 10 may then be positioned as desired with insertion tube portion 14 ready to aid the insertion of the acupuncture needle 18 positioned therewithin. The acupuncturist may then insert the needle 18 into the patient by pushing handle portion 18a of the needle 18 into the interior 34 of insertion tube portion 14, and thus causing needle portion 18b to extend beyond the end of insertion tube portion 14 and to be inserted into the patient. Insertion tube portion 14 is then withdrawn from around the inserted needle 18, and the process continued as required. When the acupuncture procedure is completed and/or container/dispenser 10 is depleted of needles 18, container/dispenser 10 may be discarded if it is economically feasible to do so, or alternatively may again be sterilized for future use and refilled with additional acupuncture needles 18.

It is to be understood that the present invention is not limited to the sole embodiment described above, but encompasses any and all embodiments within the scope of the following claims.

I claim:

1. A combination container and dispenser for the containment and storage, dispensing, and insertion of acupuncture needles having a handle portion and a shaft portion, said container and dispenser comprising a storage portion and an insertion tube portion, said storage portion having a needle installation end and closed end opposite said installation end, said insertion tube portion having an internal diameter closely fitting and allowing for the passage of said handle portion of any said acupuncture needles, said insertion tube portion extending beyond the plane defined by said closed end of said storage portion of said container and dispenser, said installation end of said storage portion having an opening for the installation of one or more said acupuncture needles therein, said storage portion having a slot extending along a top portion thereof providing for the manipulation of any acupuncture needles contained therein, said storage portion being joined with said insertion tube portion along a common side with said common side having an internal passage, said internal passage closely fitting and providing for the passage of said shaft portion of any said acupuncture needles from said storage portion to said insertion tube portion, whereby said needles may be installed within said storage portion of said container and dispenser, manipulated to and through said passage to said insertion tube portion, and passed through said insertion tube portion of said container and dispenser.

2. The container and dispenser of claim 1 wherein;

said container and dispenser is formed as a single monolithic unit.

3. The container and dispenser of claim 1 wherein; said container and dispenser is formed of stainless steel.

4. The container and dispenser of Claim 1 wherein; said storage portion of said container and dispenser contains a plurality of internal parallel depressions, said depressions extending between said installation end and said enclosed end of said storage portion, said depressions closely fitting said handle portions of said acupuncture needles, whereby said handles of said acupuncture needles may be retained in place within said storage portion of said container and dispenser.

5. The container and dispenser of Claim 1 including; a crest between said storage portion and said passage, said crest providing for the retention of said acupuncture needles within said storage portion of said container and dispenser.

6. One piece acupuncture needle handling means for use with acupuncture needles of the type having a long slender solid shank portion of small diameter at one end and a larger diameter handle portion at the other end comprising:

a magazine having means for loading single ones of said needles at a loading end, means for storing multiple said needles in a side by side relationship in an intermediate portion, and means for discharging single ones of said needles from a discharge end thereof, said magazine further having a slot along a top portion thereof which serves to expose only said handle portions of said multiple needles in said intermediate portion so that said needles may be manually moved across said intermediate portion from said loading end to said discharge end.

an ejector integral with and adjacent to said discharge end of said magazine having a dispensing end, said ejector having means for receiving a single one of said needles as it is discharged from said discharge end of said magazine, said ejector fully exposing said handle portion of said needle so as to allow for manual lengthwise pushing of said needle through said ejector and out said dispensing end thereof, said dispensing end of said ejector extending beyond the geometric extents of said magazine so as to allow for accurate placement of said needle prior to said manual pushing through said ejector.

* * * * *